(12) United States Patent
Hall et al.

(10) Patent No.: US 10,441,252 B2
(45) Date of Patent: *Oct. 15, 2019

(54) MEDICAL TOILET WITH USER CUSTOMIZED HEALTH METRIC VALIDATION SYSTEM

(71) Applicants: David R. Hall, Provo, UT (US); Dan Allen, Springville, UT (US); Min Kang, Provo, UT (US); Ben Swenson, Lehi, UT (US); Terrece Pearman, Draper, UT (US)

(72) Inventors: David R. Hall, Provo, UT (US); Dan Allen, Springville, UT (US); Min Kang, Provo, UT (US); Ben Swenson, Lehi, UT (US); Terrece Pearman, Draper, UT (US)

(73) Assignee: Hall Labs LLC, Provo, UT (US)

( * ) Notice: Subject to any disclaimer, the term of this patent is extended or adjusted under 35 U.S.C. 154(b) by 295 days.

This patent is subject to a terminal disclaimer.

(21) Appl. No.: 15/360,101

(22) Filed: Nov. 23, 2016

(65) Prior Publication Data

US 2018/0140284 A1 May 24, 2018

(51) Int. Cl.
*A61B 10/00* (2006.01)
*A61B 5/00* (2006.01)
*G16H 50/20* (2018.01)
*G16H 40/63* (2018.01)
*G16H 40/67* (2018.01)

(52) U.S. Cl.
CPC ........ *A61B 10/0038* (2013.01); *A61B 5/0002* (2013.01); *A61B 5/6891* (2013.01); *A61B 10/007* (2013.01); *G16H 40/63* (2018.01); *G16H 40/67* (2018.01); *G16H 50/20* (2018.01); *A61B 2560/0223* (2013.01)

(58) Field of Classification Search
CPC ...... G01N 33/493; G01N 33/528; E03D 9/00; E03D 11/00; Y10T 436/118339; Y10T 436/25; C12Q 1/54; C12Q 1/006; Y10S 435/97; A61B 10/007; A61B 10/0038; A61B 5/14532; A61B 5/14546; A61B 5/0024; A61B 2562/04–066
USPC .................................................. 600/300, 301
See application file for complete search history.

(56) References Cited

U.S. PATENT DOCUMENTS

| | | | | |
|---|---|---|---|---|
| 6,351,666 B1 * | 2/2002 | Cuzick | ..................... | A61B 5/04 600/301 |
| 2004/0225449 A1 * | 11/2004 | Bevilacqua | ........ | G01N 33/5088 702/20 |

(Continued)

*Primary Examiner* — David J. McCrosky

(57) ABSTRACT

We disclose a medical toilet that includes a system for interpreting measurements collected by medical devices on or in the medical toilet and for customizing the measurements to each user. The system may use information about the user to selecting which measurements to perform, select or modify parameters that apply to the measurement techniques, and select follow-up measurements that may be performed based on the first set of measurements. These decisions may be made according to the user's physical, demographic, or medical status information that may be entered into a controller connected to the medical toilet. The controller may apply a set of rules to the measurements and thereby determine a value which provides an estimate of the validity of the measurements and which may be used to make adjustments to subsequent measurements.

20 Claims, 7 Drawing Sheets

(56) References Cited

U.S. PATENT DOCUMENTS

| | | | | |
|---|---|---|---|---|
| 2005/0261605 A1* | 11/2005 | Shemer | ............... | A61B 10/007 600/573 |
| 2012/0262298 A1* | 10/2012 | Bohm | ............... | G01N 27/3274 340/604 |
| 2014/0012116 A1* | 1/2014 | Okuyama | ............ | G01N 33/487 600/347 |
| 2015/0164343 A1* | 6/2015 | Huang | ............... | A61B 5/02055 600/301 |

\* cited by examiner

MEDICAL TOILET WITH USER CUSTOMIZED HEALTH METRIC VALIDATION SYSTEM

BACKGROUND

Field of the Invention

This invention relates to systems for determining health conditions.

Background of the Invention

Every method of measuring physiological functions has inherent limitations. Medical devices and laboratory assays may provide inaccurate results for various reasons including user error, damaged components, or attempts to use the device or assay under conditions for which it was not designed. There are also circumstances under which the medical device or laboratory assay provides data that may not be properly interpreted without knowing specific information about the patient which puts the data in proper context. Furthermore, calculated health indices, for example, Body Mass Index (BMI), are not meaningful for all body types. Additionally, health care providers sometimes simultaneously use multiple clinical measurements, each associated with a different degree of accuracy and relevance to a particular patient, to create a complex assessment of an individual's health or to select a single diagnosis out of a lengthy differential diagnosis. Each measurement may have a different shortcoming that must be taken into account when interpreting the data generated by the measurement. Included in the shortcomings are that the healthcare provider must be aware of inherent instrumental error, interpret the results based on the patient's physical status including body type, medical diagnosis, and current medications, and be aware of the instrumental error associated with a particular measurement event. The latter error may be related to the user's physical status and is particularly difficult for a healthcare provider to estimate when viewing measurement results. This is, at least in part, because the healthcare provider that conducted the measurement may not be the same healthcare provider that analyzes the results. Consequently, the healthcare provider analyzing the results may be unaware of difficulties that occurred during the measurement process. For example, with the growing use of telemedicine, a specialist may consult on a patient he or she has never met. A way to determine the level of accuracy of health-related data, select measurements that are relevant to the particular patient, and to put the data in proper context based on the user's physical status is needed.

BRIEF SUMMARY OF THE INVENTION

We disclose a medical toilet that collects measurements pertaining to a user's health status and which includes a system for identifying the level of validity of the measurements. The system is customized to each user based on physical and demographical information and medical history. The system includes a controller which receives information about a user's physical, demographical, and medical status. The medical toilet may conduct a first measurement which is relevant to the user's health and a second measurement which is an indicator of the validity of the first measurement. The controller may select the type or measurement techniques, the anatomical location from which the measurements are taken, and it may modify the parameters of the instruments taking the measurements all based on the information stored about the user in the controller. The first and second measurements may be analyzed according to at least one set of rules which assign a weight value to the first measurement.

The first and second sets of rules may also vary depending on the user's physical, demographical, and medical status information stored in the controller, including, but not limited to body type, gender, skeletal structure (fine or heavy), medical diagnosis, and current medications. The information may determine which of a plurality of sets of rules are applied to the measurements. New physical status information about the user may be periodically entered into the controller to trigger an alternative set of rules. The system may trigger the collection of a follow-up measurement, which may confirm or contradict the first measurement. Furthermore, the controller may select the follow-up measurement based on the user's physical, demographical, and medical status information.

Some embodiments of the medical toilet may transmit the measurements and calculations to a network database. A healthcare provider may download the data to a user's medical file. Changes to the user's physical status may be transmitted to the medical toilet from a controller located at a remote location so that the medical toilet continues to select the proper measurements, parameters, and rules to apply to collected data.

In addition to interpreting measurements based on a user's physical characteristics, this system adjusts the measurements themselves, including how they are taken with relation to the user's anatomy, the parameters of the instrumentation, as well as assessing the validity of the measurement to provide a customized set of measurements. Initial measurements are adjusted based on input about a user's physical, demographic, and medical status, their validity assessed, then more measurements may be taken with further adjustment. Both the validity of the measurement and the relevance to the user is thereby optimized.

DETAILED DESCRIPTION OF THE INVENTION

Definitions

Figure 1:
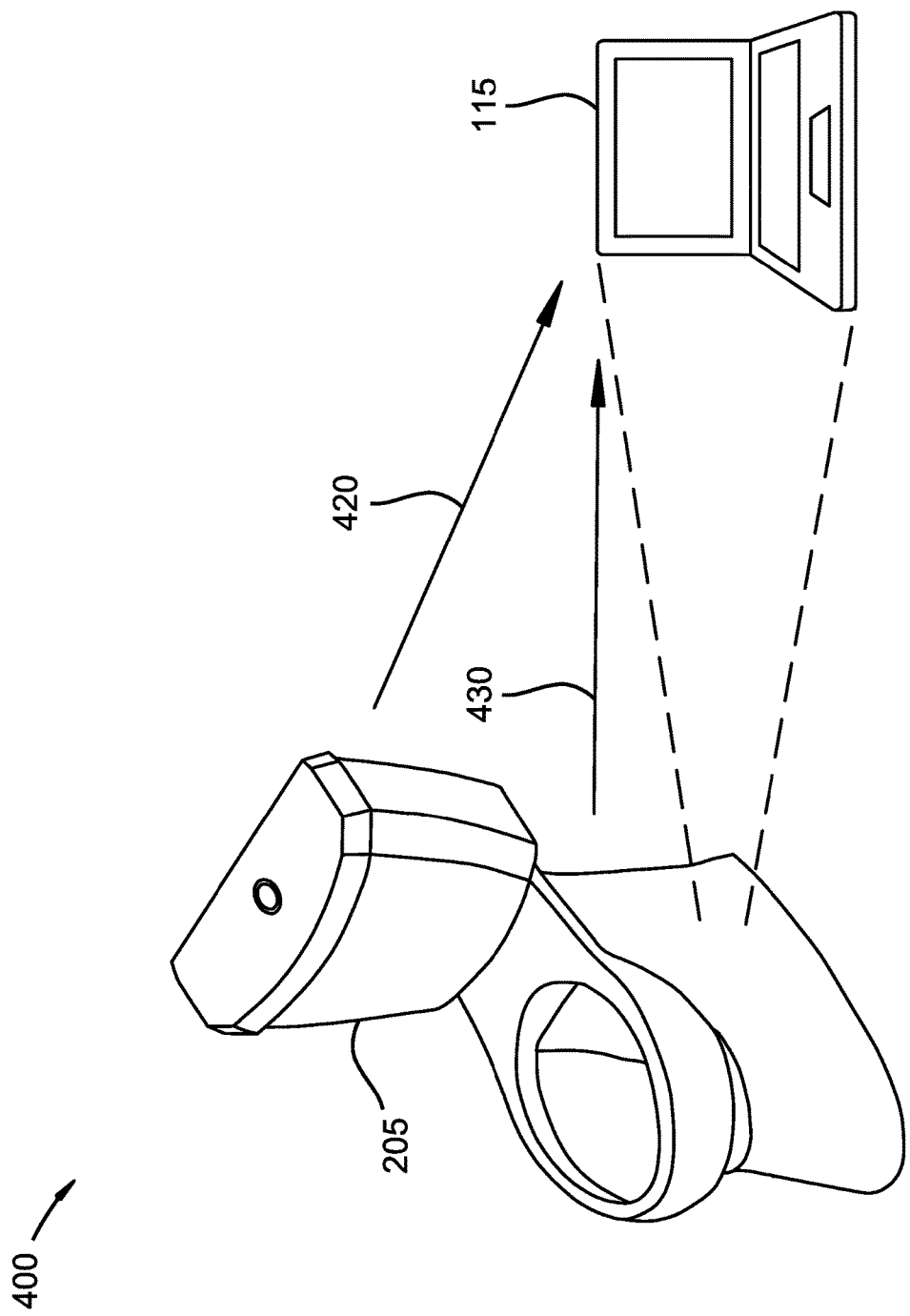
FIG. 1 is a perspective view of an embodiment of the invention in which a first and second measurement are collected by a medical toilet and the data is transferred to a controller.

Toilet, as used herein, means a device that collects biological waste products of a mammal, including urine and feces.

Medical toilet, as used herein, means a toilet that conducts one or more measurements relevant to a user's health status. This may include, but is not limited to, quantification of analytes in urine or feces, cardiovascular parameters, bioimpedance measurements, and body weight.

Health status, as used herein, means the current physiological state of a mammal, particularly with regard to disease status or injury. In general, this term refers to the overall health of the mammal. However, individual parameters relating to a specific body part or biological system may be measured for the purpose of diagnosing disease states or identifying physiological characteristics or functions that are outside of the normal range. Such individual physiological characteristics or functions may be used to define the health status of the mammal with regard to a specific physiological system.

User, as used herein, means any mammal, human or animal, for which the medical toilet disclosed herein is used to measure physiological functions which may be used to assess the mammal's health status.

Healthcare provider, as used herein, means any individual who performs a task, mental or physical, in relation to health-related services provided to a user. In addition to clinicians who practice medicine directly on a user, the term healthcare provider includes any person that enters data into a computer, when the data entry is used in analysis of a user's health status or to improve a user's health.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

Disclosed herein is a method and apparatus for using a medical toilet to conduct customized measurements that provide information about a user's health status. Importantly, the toilet includes a system for customizing the measurements for each user, validating the accuracy of the measurements, and both selecting and performing follow-up measurements that may be needed. The system uses physical, demographical, and medical status information about the user, not just to interpret the measurements, but to make adjustments within the medical toilet and instruments therein to optimally perform the measurements for each user. The physical, demographic, and medical status information may include a body type, including, but not limited to, endurance athlete, weight bearing athlete, non-athlete, male, female, under a defined age, over a defined age, fine skeletal structure, and heavy skeletal structure. The medical status information may also comprise a medical diagnosis and the user's current medications, each of which, may impact reasonable interpretation of the measurements, alter which measurement is most useful for the specific user, and the parameters under which the measurement is taken.

Medical devices are typically designed to be used in the same way for each user. However, in some instances, the optimal parameters to conduct a measurement with a particular medical device vary from user to user. Examples of parameters that may be adjusted based on physical, demographic, and medical status information include, but are not limited to, power level, wavelength of a light source in a spectroscopy instrument, frequency of alternative current electric field, instrument sensitivity, instrument dynamic range, length of measurement time, applied voltage, anatomical location at which the first or second measurement is taken, sample rate, sample volume, and data filter bandwidth. A controller within or connected to the medical toilet may use the physical, demographical, and medical status information to predict the optimal parameters to use with each instrument when collecting measurements for a particular user.

In addition to the parameters used to perform a measurement, often, the type of measurement that is optimal for a user varies according to physical, demographic, or medical status. For example, reliable bioimpedance measurements taken from the thigh may be difficult to obtain from obese users. Therefore, measuring bioimpedance from a different anatomical site on an obese user or conducting a measurement other than bioimpedance may yield more a more useful measurement. In other example, a measurement that requires a user to remain still for a length of time may be suboptimal for young children. In still another example, a user whose disease status or medications cause the user to have a faint pulse. This user may need to have a heart rate measured through the carotid artery, which typically gives a strong signal as compared to the wrist, to acquire a meaningful heart rate measurement.

According to an embodiment of the invention, the validity of a first measurement is assessed by conducting a second measurement. A general explanation of the method to determine the validity of the first measurement is provided in Applicant's U.S. patent application Ser. Nos. 15/270,674 and 15/279,734 which are hereby incorporated by reference in their entirety. A first set of rules may be applied to the first and second measurements which results in a weight value. The weight value is assigned to the first measurement and may be a function of the second measurement. A second set of rules may be applied to the first measurement and the weight value to calculate an indicator value. The indicator value assigns an estimate of validity to the first measurement and, consequently, informs its relevance to a user's health status. The second set of rules may define a threshold value for the weight value and may signal the controller to flag the first measurement as invalid or to be excluded from multi-variable calculations that provide an assessment of the user's health status. A clinician may choose to interpret a first measurement that has a mid-range indicator value in combination with more reliable measurements to bolster the validity of a general trend shown by the first measurement. Thus, the first measurement may provide some value but is not assigned more relevance than it merits. The rule sets may vary for each user as a function of the physical, demographical, and medical information stored in the controller for that user. This is at least because a measurement that may seem suspect for one user may be expected for another user depending on physical, demographical, or medical differences between the two users. Thus, the estimate of validity may be dependent on the physical, demographical, and medical information provided for the user.

Referring now to the figures, FIG. 1 illustrates an embodiment of the customized measurement validation system 400, which is an embodiment of the disclosed invention. In this embodiment, both first measurement 420 and second measurement 430 are collected by medical devices within medical toilet 205. The arrows indicate that first and second measurements 420 and 430 are transmitted to controller 115. Controller 115 then applies the first and second rule sets based, at least in part, on a user's physical and demographical status information. The rule sets controller 115 applies may be selected based on the physical and demographic status information and may vary with each user. The dashed lines indicate that, in this embodiment, computer 115 is positioned within medical toilet 205. While schematically depicted as a laptop computer, computer 115 may be a controller on or within the medical toilet, a server, a computer in a healthcare facility, or any other computing device that may receive and store data, be programed to perform calculations on the data, and provide an output of the calculated data.

While FIG. 1 illustrates a single first measurement and a single second measurement, multiple second measurements may be collected and used as described herein to assess the validity of the first measurement. Alternatively, a single second measurement may be used to assess the validity of multiple first measurements. The single or multiple first and second measurements may be selected by the controller based on the user's physical, demographic, and medical status information.

Medical toilet 205 may conduct a plurality of measurements including, but not limited to, body temperature, body weight, body composition (i.e. percent body fat, intracellular and/or extracellular water), heart rate, pedal pulse rate, blood pressure, blood oxygen saturation, electrocardiogram measurement, urine constituents and parameters including urine color, glucose, urea, creatinine, specific gravity, urine protein, electrolytes, urine pH, osmolality, human chorionic gonadotropin (for detecting pregnancy), hemoglobin, white blood cells, red blood cells, ketone bodies, bilirubin, urobilinogen, free catecholamines, free cortisol, phenylalanine, and urine volume. The measurements may also include fecal analysis including fecal weight and volume, calprotectin, lactoferrin, hemoglobin, stress test, blood pressure, hematocrit, serum insulin level, hemoglobin A1c, breathing rate, blood urea nitrogen, serum creatinine, alanine aminotransferase, aspartate aminotransferase, alkaline phosphatase, serum bilirubin, serum total protein, serum albumin, serum gamma-glutamyl transpeptidase, prothrombin time, Holter monitoring, serum levels of a pharmaceutical product, and serum levels of a metabolite of a pharmaceutical product. Additionally, sensors that measure flow, volume, or weight may determine periods of excretion activity to measure, for instance, urination or defecation exertions, or selectively record measurements that were collected during periods of low exertion. These measurements are useful because certain other measurements are best performed after complete voiding of the bowel and bladder for maximum accuracy.

Figure 2:
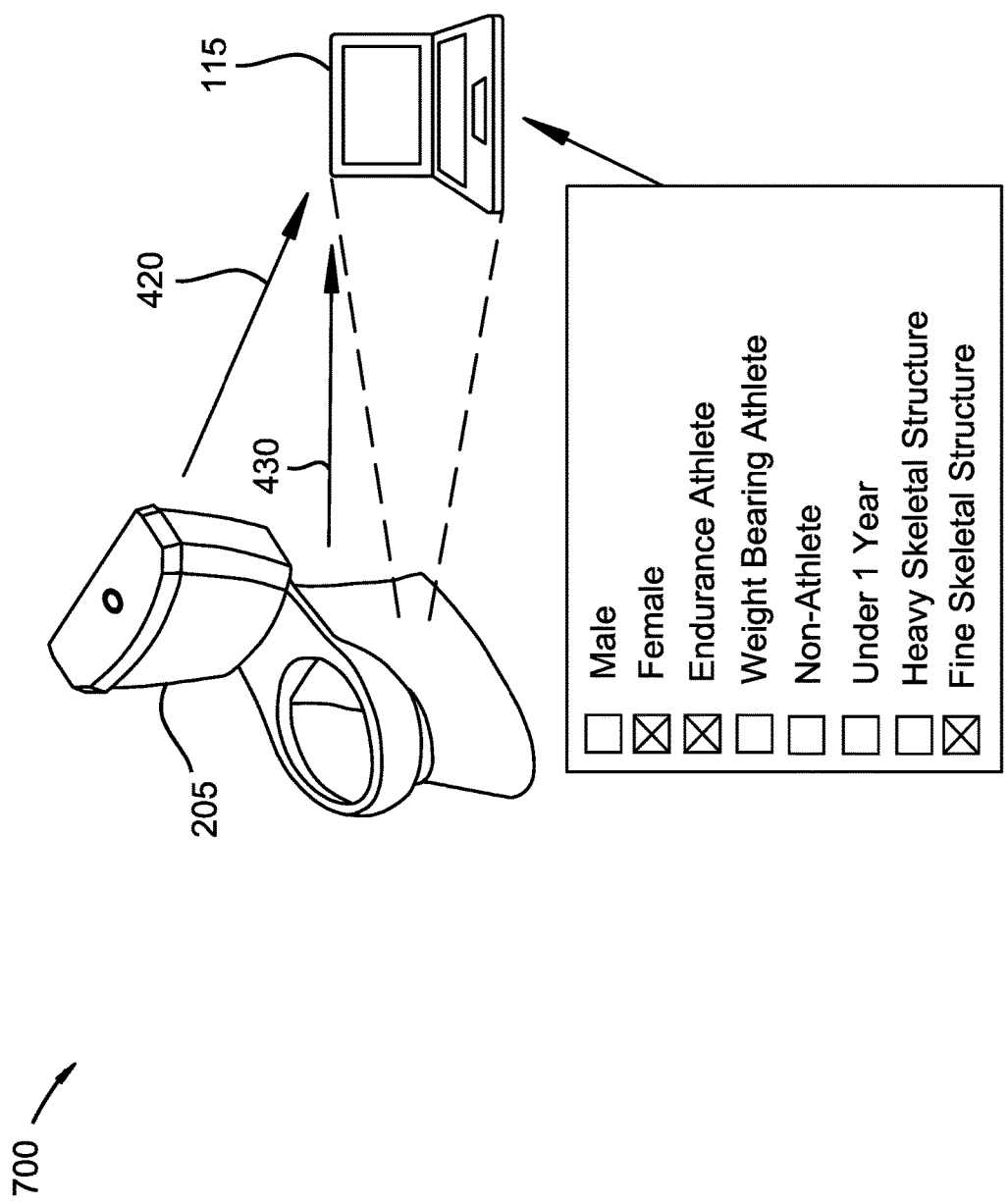
FIG. 2 is a perspective view of an embodiment of the invention in which user information is entered into the controller of a medical toilet and both a first and second measurement are collected by a medical toilet.

FIG. 2 illustrates an embodiment of the customized measurement validation system 700. FIG. 2 shows a user's physical, demographic, and medical status information, which indicates that the user is a female endurance athlete with a fine bone structure. This information is entered into controller 115 and stored in a user information file. As described elsewhere herein, different physiological characteristics associated with a user may impact the most accurate and meaningful interpretation of the first health measurement as well as which measurements should be collected for that user and their optimal collection parameters. The controller uses this information to select appropriate measurements and appropriate collection parameters for performing the measurements for this user. The controller then applies the appropriate set of rules based on the user's physical, demographic, and medical status information to assess the validity of the first measurement.

Figure 3:
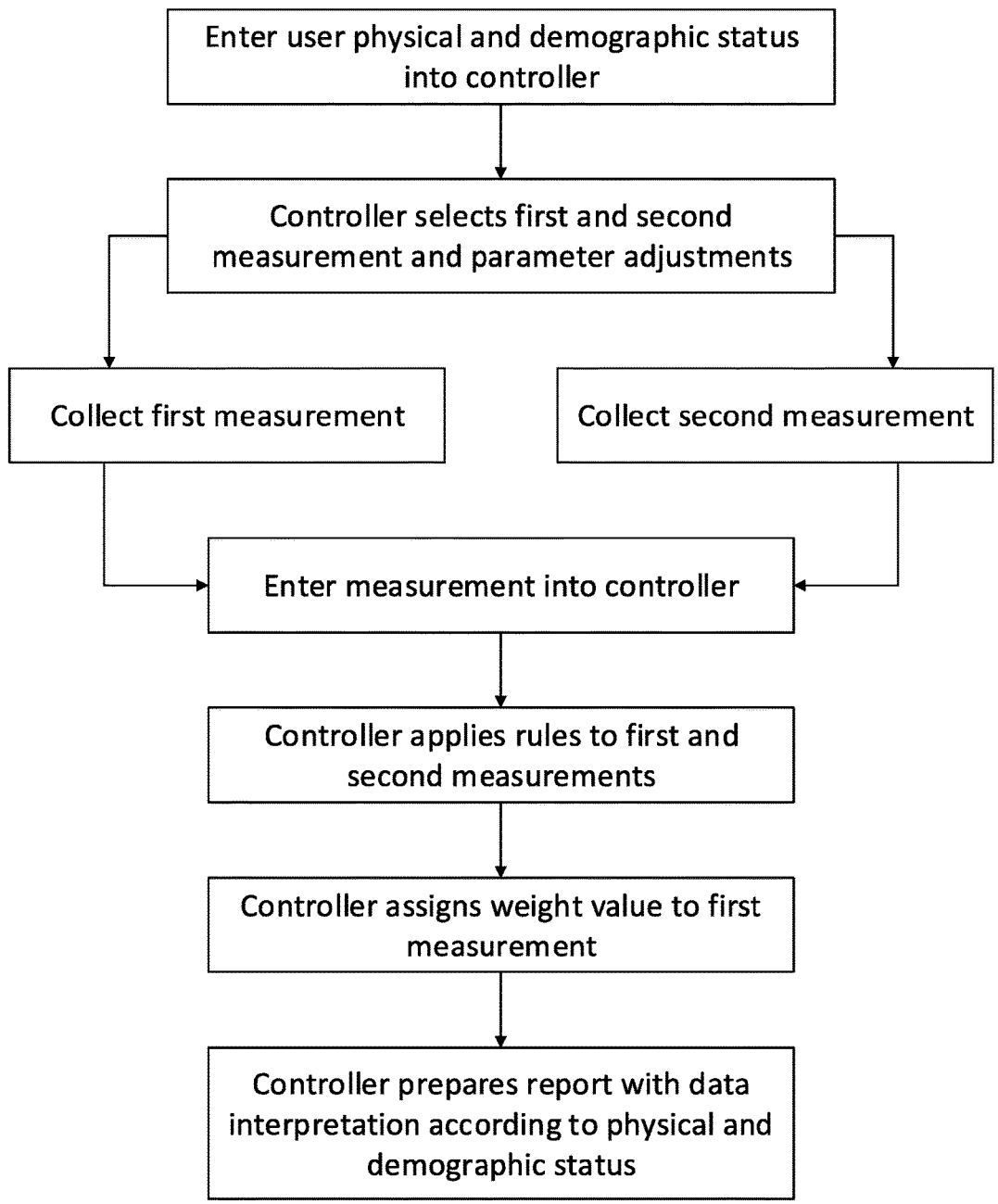
FIG. 3 is a flow chart illustrating an embodiment of the invention in which the controller calculates a numerical indicator of the validity of the first measurement.

FIG. 3 is a flow chart illustrating a method of using an embodiment of the customized measurement validation system. The embodiment includes a controller into which the user's physical, demographic, and medical status information is entered and stored. This step may occur by manual data entry or a variety electronic transmission methods known in the art. The controller analyzes the physical, demographic, and medical status stored in the information file and uses it to select an optimal first measurement to assess a particular physiological function. The controller also selects a second measurement for validating the first measurement and also determines parameter adjustments that may be used to optimize the first and second measurements. These may also be based on the controller's analysis of the user's physical, demographic, and medical status in the information file. The first and second measurements are transferred into the controller and the controller applies a first and second rule sets to the first and second measurements. The rule sets may be chosen based on the user's physical, demographic, and medical status in the user information file. The controller assigns an indicator value to the first measurement which is determined by the application of the rule sets, is a function of the second measurement, and which is an indication of the validity of the first measurement. A healthcare provider may use this indicator value to make a decision about the use of the first measurement. For example, the healthcare provider may decide to use the first measurement as an indicator of a user's health status, to consider the first measurement but conduct further clinical investigation, or to ignore the first measurement as an inaccurate data point.

Figure 4:
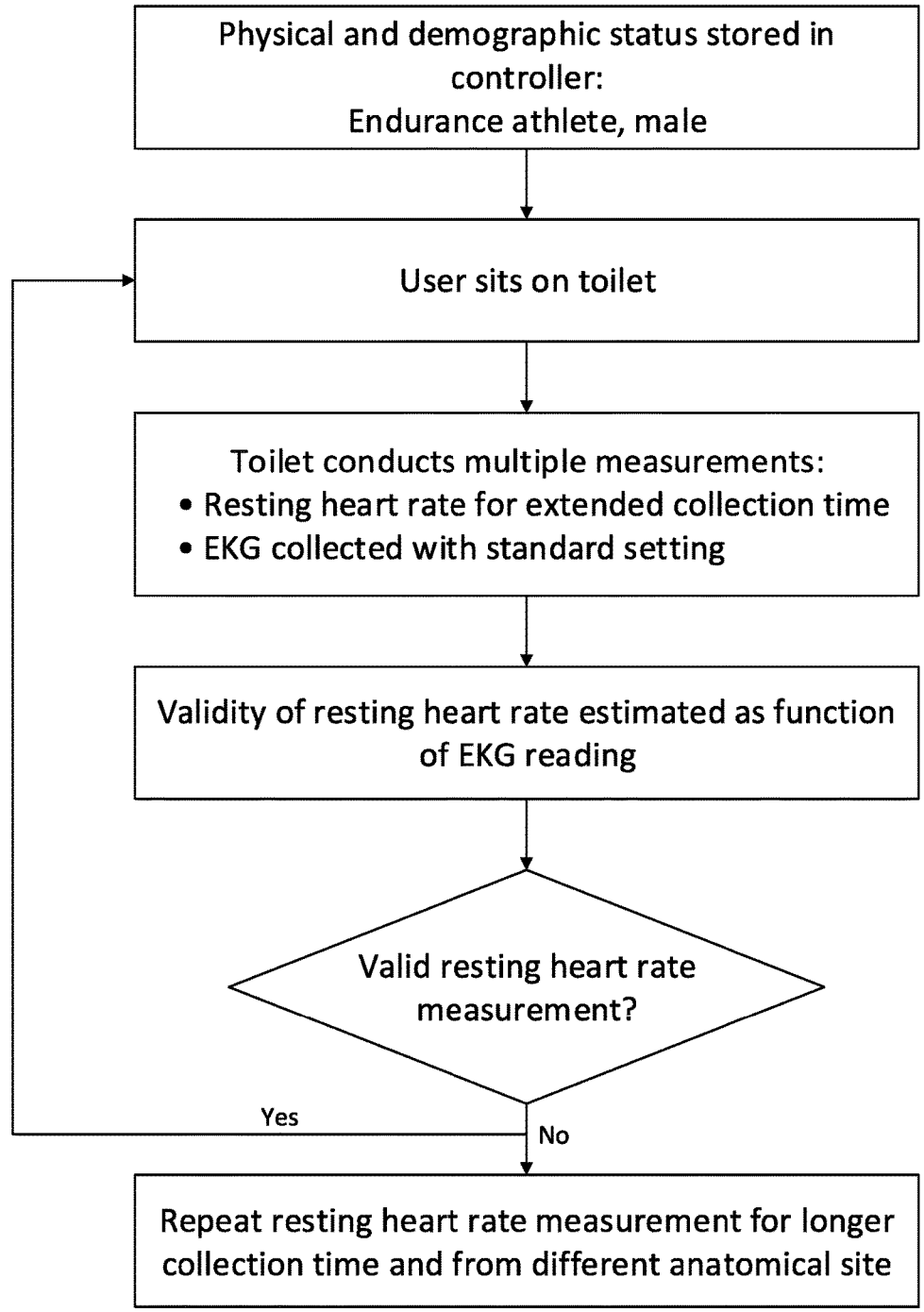
FIG. 4 is a flow chart illustrating an example of a method of use of an embodiment of the invention in which user information is entered into the controller, measurements are conducted, and modifications of the measuring technique are made with reference to the user information.

FIG. 4 is a flow chart illustrating how a measurement parameter may be adjusted according to an embodiment of the invention. FIG. 4 illustrates the step of entering information about the user into the user information file in the controller. In this case, the information includes the fact that the user is a male endurance athlete. This information suggests that the user may have a low percent body fat, significant muscle tone, and, in particular, a low resting heart rate. The user sits on the medical toilet which conducts measurements that include a resting heart rate measurement (the first measurement) and an electrocardiogram (EKG) reading (the second measurement). Because the user is an endurance athlete, the controller instructs the toilet to extend the time of collection of the resting heart rate measurement in order to collect a statistically significant number of cardiac contraction events. The two measurements are transmitted to the controller which uses the EKG reading to determine the validity of the resting heart rate measurement. If the resting heart rate measurement is assigned an indicator value that suggests a valid measurement, the controller may store this information. The next time the same user requires a resting heart rate measurement, the controller may signal the medical toilet to conduct the measurement under the same parameters. Alternatively, if the indicator value suggests that the resting heart rate measurement as conducted did not result in a valid measurement, the controller may signal the medical toilet to adjust the parameters under which the measurement is taken and repeat the measurement using the modified parameters. In this example, the controller signaled the medical toilet to both lengthen the collection time and measure the resting heart rate through a different part of the user's body. If these parameters are successful, the controller will record them and the next resting heart rate measurement for this user may be conducted according to the second set of parameters. Consequently, the system is able to "learn" the best method to measure a particular physiological event for each user.

Figure 5:
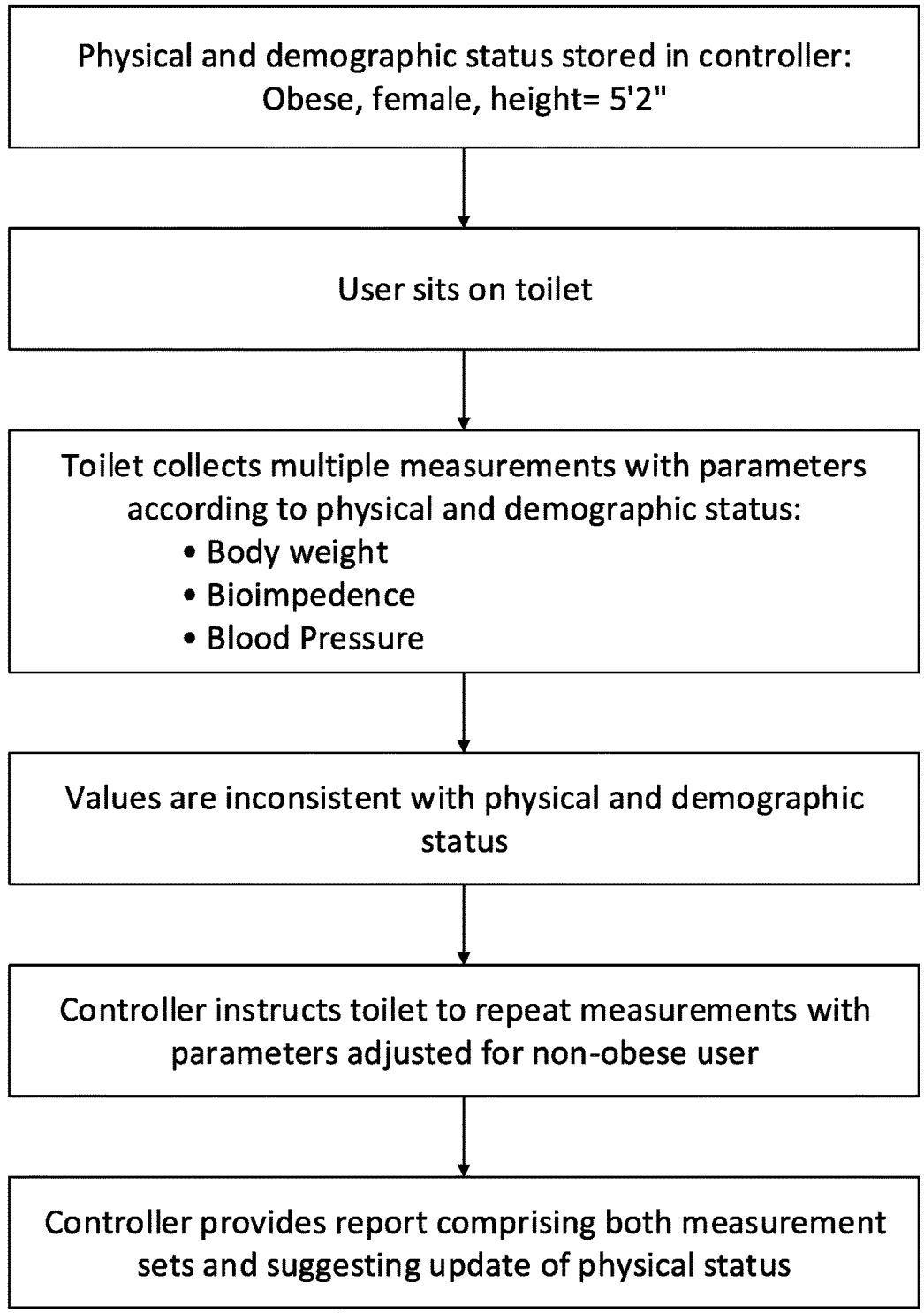
FIG. 5 is a flow chart illustrating an example of the use of an embodiment of the invention in which updated user information is needed.

FIG. 5 illustrates a scenario in which the measurements produced data that are significantly inconsistent with the physical, demographical, and medical status information stored in the user information file for that user. The physical, demographical, and medical status information that is stored in the user information file indicates that the user is an obese female whose height is 5 foot 2 inches. The user sits on the medical toilet and the controller signals the medical toilet to measure bioimpedance, body weight, and blood pressure. The data collected by the measurements are transmitted to the controller. The controller analyzes the measurements and determines that the values are not consistent with those expected for an obese female whose height is 5 foot 2 inches. For example, the measurements may have indicated that the user's body weight is 120 pounds, her blood pressure is within the lower end of the normal range for a healthy adult, and a body fat calculation may have provided a low value. The controller may then instruct the medical toilet to repeat the measurements using parameters that it would have selected for a non-obese user. The controller may provide a report which includes both sets of measurements, noting the inconsistency with the physical, demographical, and medical status information provided for that user in her user information file. The controller may also suggest that the physical, demographical, and medical status information in that user's user information file should be updated (perhaps the user lost significant body fat) or that the wrong user identification information was entered prior to performing the measurements. Thus, not only may an improper interpretation of the data have been avoided, but an error in medical recordkeeping may have been avoided. For example, if the controller was connected to a computerized medical recordkeeping system, an incorrect user identification could have caused the measurements to be stored in the wrong patient file.

Figure 6:
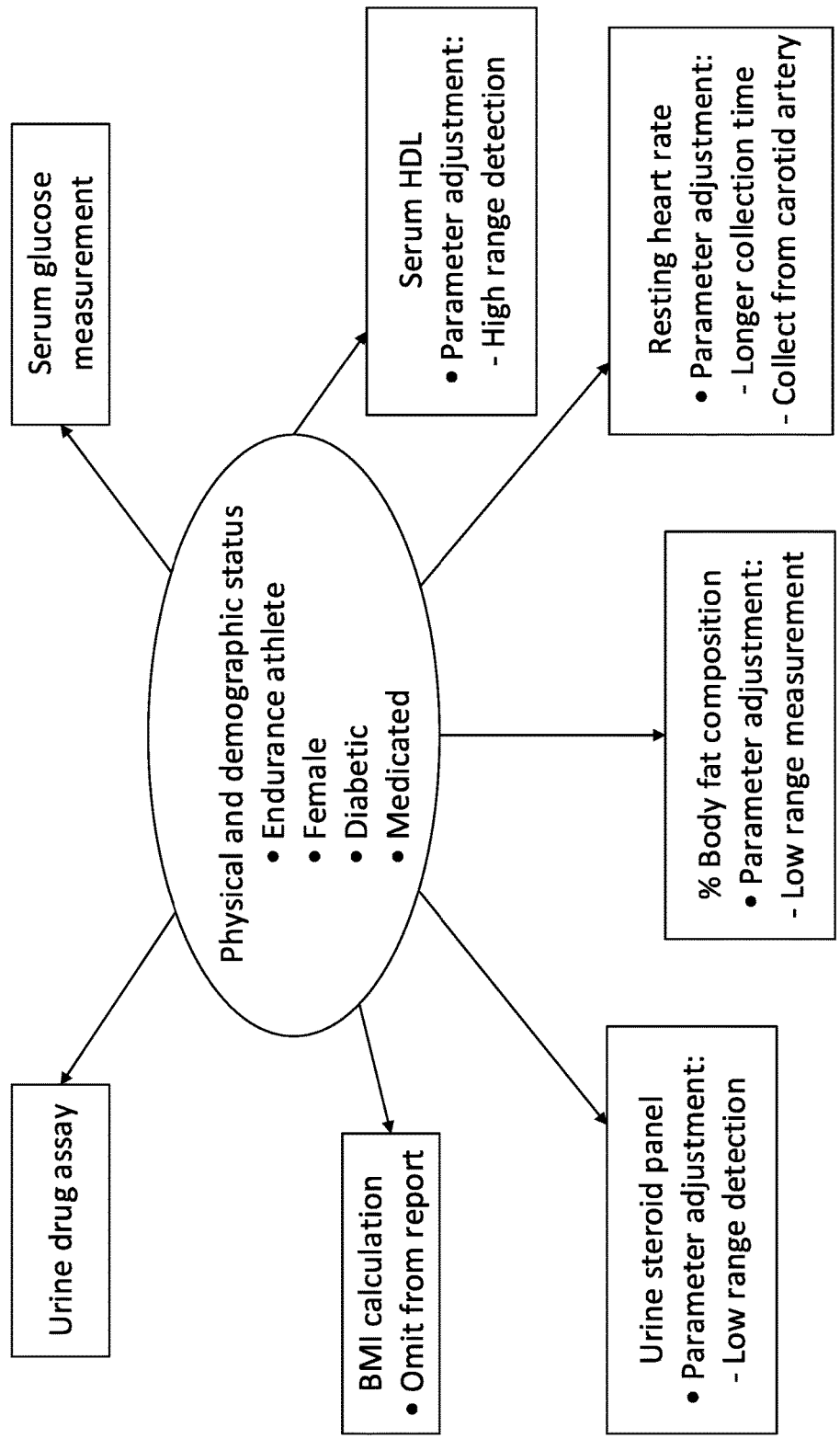
FIG. 6 is a diagram illustrating an embodiment of the invention in which the controller selects measurements, modifies the parameters for collecting some measurements, and determines which calculations to perform based on user information.

FIG. 6 is a diagram illustrating a scenario in which the controller uses physical, demographical, and medical status in the user information file to select appropriate measurements, to select appropriate calculations to be performed using the data collected by the measurements, as well as appropriate adjustable parameters to use when conducting the measurements. In the example of FIG. 6, the user is a female endurance athlete who is diabetic and on medication for her diabetes. One of the chosen measurements is resting heart rate. As discussed in reference to the example of FIG. 4, an endurance athlete may have a low resting heart rate. For this reason, the controller adjusts the parameters of the measurement to increase the time the heart rate is measured and to measure the heart rate in the user's neck where the carotid artery is located. The carotid artery is expected to give a stronger signal than other parts of the body. A female endurance athlete often has reduced levels of steroid hormones which may interfere with normal menstrual cycling and fertility. For this reason, the controller signals the toilet to measure urine steroid hormones and to adjust the parameters to accurately measure within a lower than normal range of detection. This user is likely to have a low percent body fat so the measurements that will be used to calculate body fat will also be adjusted to accurately measure within a low range of detection. An athlete is likely to have elevated serum high density lipoproteins (HDL) so the parameters are adjusted to accurately measure HDLs in the upper range. Body mass index (BMI) is not meaningful for very fit individuals so this calculation is not performed or reported. Finally, because the user is a diabetic and medicated for her diabetes, the controller signals the medical toilet to measure serum glucose levels and quantify the amount of her medication or metabolites thereof in her urine. The latter may be used to confirm drug compliance or, along with serum glucose levels, to assess the appropriateness of her prescribed drug and its dosage.

Figure 7:
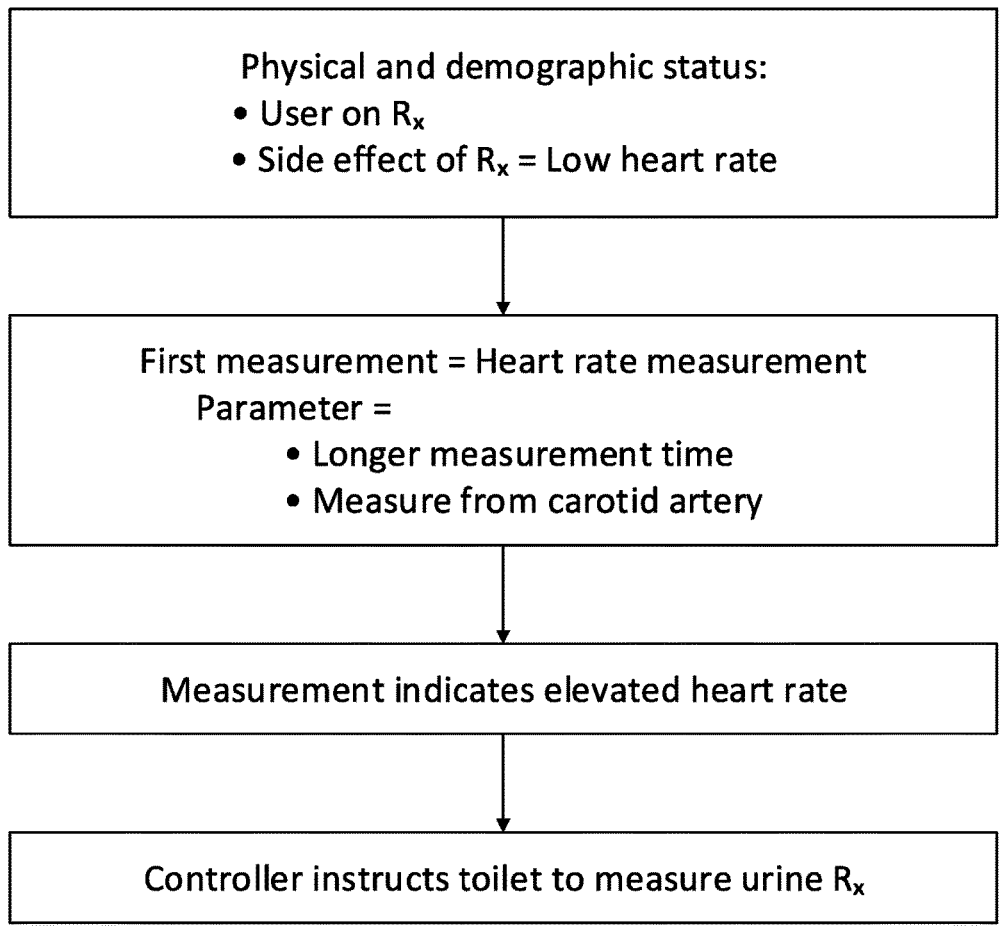
FIG. 7 is a flow chart illustrating a process according to an embodiment of an invention in which the toilet conducts follow-up measurements in response to a first measurement and a user's medical history.

FIG. 7 is a flow chart illustrating a method of using an embodiment of the invention to confirm drug compliance and appropriateness of dosage. The physical, demographical, and medical status stored in the user's user information file in the controller indicates that the user is on a prescription medication that has a common side effect of lowered heart rate. Therefore, the controller selects a heart rate measurement for this user to determine if the drug has lowered the user's heart rate to an unsafe level. The chosen parameters are an extended measurement time and collection from the user's neck near the carotid artery in an attempt to get a valid measurement from a user that may have a slow heart rate. However, the heart rate measurement indicates that the user has an elevated heart rate. This is an unexpected result for a user who is currently taking this drug. Consequently, the controller signals the medical toilet to measure the presence of the user's drug or metabolites thereof in the user's urine. If the urine analysis indicates low or absent drug in the user's body, the controller may provide a report suggesting that the user has not taken the medication, the dosage is too low, or a different medication may be appropriate.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:
1. A medical toilet comprising:
   a toilet comprising:
      a first medical device; and
      a second medical device,
   wherein the first medical device performs a first measurement according to a first adjustable parameter and the second medical device performs a second measurement according to a second adjustable parameter; and
   a health measurement management system disposed on or in the toilet, the health measurement management system comprising:
      a controller, the controller comprising a non-transitory computer readable medium and a memory, wherein the memory stores:

a user information file, wherein the user information file comprises one or more of the following: a physical status, a demographic status, and a medical status;

a first result, wherein the first result is collected by the first measurement; and a second result, wherein the second result is collected by the second measurement;

wherein the controller selects the first measurement and the second measurement according to one or more of the user's physical status, the demographic status, and the medical status, wherein the controller selects a first setting for the first adjustable parameter and a second setting for the second adjustable parameter, each according to one or more of the user's physical status, the demographic status, and the medical status, wherein the controller calculates a numerical estimate of validity of the first result by applying at least one set of rules to at least one of the first result and the second result, and wherein the controller selects the at least one set of rules according to one or more of the user's physical status, the demographic status, and the medical status.

2. The medical toilet of claim 1, wherein the first adjustable parameter and the second adjustable parameter are independently selected from the following:

a power level, a wavelength of a light source in a spectroscopy instrument, a frequency of an alternative current electric field, an instrument sensitivity, an instrument dynamic range, a length of measurement time, an applied voltage, an anatomical location at which the first or second measurement is taken, a sample rate, a sample volume, and a data filter bandwidth.

3. The medical toilet of claim 1, wherein the user information file includes at least one value collected by one or more physical and physiological measurements.

4. The medical toilet of claim 1, wherein the user information file includes a medical diagnosis.

5. The medical toilet of claim 1, wherein the user information file includes at least one body type.

6. The medical toilet of claim 5, wherein the at least one body type comprises one or more of the following: endurance athlete, weight bearing athlete, non-athlete, male, female, under a defined age, over a defined age, fine skeletal structure, and heavy skeletal structure.

7. The medical toilet of claim 1 wherein the user information file includes a list of the user's current medications.

8. The medical toilet of claim 1, wherein at least one of the first medical device and the second medical device measures one or more properties of a user's biological waste.

9. The medical toilet of claim 8, wherein the at least one property of the user's biological waste is selected from one or more of the following:

urine color, urine glucose concentration, urine urea concentration, urine creatinine concentration, urine specific gravity, urine protein concentration, urine electrolyte concentrations, urine pH, urine osmolality, urine human chorionic gonadotropin concentration, urine hemoglobin level, white blood cells in urine, red blood cells in urine, urine ketone body concentration, urine bilirubin concentration, urine urobilinogen concentration, urine free catecholamine concentration, urine free cortisol concentration, urine phenylalanine concentration, urine volume, fecal volume, fecal weight, fecal calprotectin level, fecal lactoferrin level, fecal hemoglobin level, urine levels of a pharmaceutical compound, urine levels of a metabolite of a pharmaceutical compound, fecal levels of a pharmaceutical compound, and fecal levels of a metabolite of a pharmaceutical compound.

10. The medical toilet of claim 1, wherein the first measurement and the second measurement are independently selected from the following:

electrocardiogram analysis, heart rate, stress test, blood pressure, hematocrit, serum insulin level, hemoglobin A1c, breathing rate, blood urea nitrogen, serum creatinine, alanine am inotransferase, aspartate aminotransferase, alkaline phosphatase, serum bilirubin, serum total protein, serum albumin, serum gamma-glutamyl transpeptidase, prothrombin time, Holter monitoring, serum levels of a pharmaceutical product, serum levels of a metabolite of a pharmaceutical product, and bioimpedance measurements.

11. The medical toilet of claim 1, wherein the controller records a first setting for a first adjustable parameter and a second setting for a second adjustable parameter for the user and applies the first and second settings during a subsequent session with the user in which the first and second measurements are performed.

12. The medical toilet of claim 1 wherein the controller analyzes a first result and a second result according to a plurality of instructions provided by the non-transitory computer readable medium, and wherein the controller signals the medical toilet to collect at least one follow-up measurement.

13. The medical toilet of claim 12, wherein the at least one follow-up measurement comprises the first measurement, wherein the first medical device performs the first measurement with a first modification to the first adjustable parameter.

14. The medical toilet of claim 13, wherein the controller signals the medical toilet to perform the first measurement with the first modified setting during a subsequent session with the user.

15. The medical toilet of claim 12, wherein the at least one follow-up measurement comprises the second measurement, wherein the second measurement is performed with a second modification to the second adjustable parameter.

16. The medical toilet of claim 12, wherein the controller signals the medical toilet to perform an identical at least one follow-up measurement during a subsequent measurement session with the user during which the first and second measurements are performed.

17. The medical toilet of claim 1, wherein the controller performs at least one calculation comprising the first result according to a plurality of instructions provided by the non-transitory computer readable medium.

18. The medical toilet of claim 17, wherein the controller selects the at least one calculation according to one or more of the user's physical status, the demographic status, and the medical status.

19. The medical toilet of claim 17, wherein the controller generates a report comprising the first result and the numerical estimate of validity according to a plurality of instructions provided by the non-transitory computer readable medium.

20. The medical toilet of claim 1, wherein the controller transmits the first result, the second result, and the numerical estimate of validity to a network database.

* * * * *